United States Patent
Pugh

(12)
(10) Patent No.: US 7,668,734 B2
(45) Date of Patent: Feb. 23, 2010

(54) INTERNET MEDICAL INFORMATION SYSTEM (IMED)

(76) Inventor: Timothy Pugh, 170 Huntington Dr., Virginia Beach, VA (US) 23462

( * ) Notice: Subject to any disclaimer, the term of this patent is extended or adjusted under 35 U.S.C. 154(b) by 655 days.

(21) Appl. No.: 11/400,903

(22) Filed: Apr. 10, 2006

(65) Prior Publication Data

US 2006/0229919 A1  Oct. 12, 2006

Related U.S. Application Data

(60) Provisional application No. 60/669,069, filed on Apr. 8, 2005.

(51) Int. Cl.
```
G06Q 10/00      (2006.01)
G06Q 50/00      (2006.01)
A61B 5/00       (2006.01)
G06F 19/00      (2006.01)
```
(52) U.S. Cl. .............................................. 705/2; 705/3
(58) Field of Classification Search ..................... 705/2, 705/3, 4
See application file for complete search history.

(56) References Cited

U.S. PATENT DOCUMENTS 6,044,349 A * 3/2000 Tolopka et al. ................. 705/1

* cited by examiner

Primary Examiner—Gerald J. O'Connor
Assistant Examiner—Amber L Altschul
(74) Attorney, Agent, or Firm—Robert M. M. Seto

(57) ABSTRACT

A system for creating, maintaining and selectively accessing medical histories. The system allows a patient and other selected parties to build a medical history, but importantly places the authority to grant access to the medical history solely in the hands of the patient. When the patient's medical history file is created, the patient also pre-authorizes selected parties, including government agencies such as FEMA to have access to at least part of the patient's history. Each selected party is associated with an access module that dictates the level of access the party has to the medical history. Primary care physicians are associated with a full access module, which allows full access to the patient's medical history. Dentists and pharmacies are associated with a limited access module, which limits the party's access to only pertinent portions of the patient's medical history. The present system also includes a fingerprint scanner and/or retina scanner that can be used to identify unconscious patients and patients without an I.D. card.

19 Claims, 6 Drawing Sheets

600

IMED Catastrophe Report (Sample FEMA information)

605

Patient's Name and Location

610

Patient's 5-day Medical Requirements

615

Patient's Basic Report

620

Patient's Emergency Contact Info.

Figure 6

INTERNET MEDICAL INFORMATION SYSTEM (IMED)

The present invention was originally disclosed in U.S. provisional patent application Ser. No. 60/669,069 filed on Apr. 8, 2005, and priority is claimed to the provisional patent application.

BACKGROUND OF THE INVENTION

The present invention relates generally to the fields of electronic data storage and privacy, and more specifically to controlling access to sensitive electronic files such as a person's medical history.

Proper medical diagnosis and subsequent treatment of a patient requires that medical care providers know specific facts regarding the patient's medical history, and have access to lab results, in a timely manner. The medical history assists the medical provider in evaluating a current medical problem and alerts the medical care provider to allergies, side effects of medications, and other potential scenarios, the knowledge of which is critical in treating the patient. A traditional medical history includes a list of the patient's major illnesses, or diseases, such as heart disease or diabetes, results of recent lab tests, including EKG's, current and past medications, known allergies, date last seen by the medical care provider, dates of last prescriptions and reasons for prescribing, and whether the reasons for prescribing constituted temporary or continuing conditions. It is also important that the medical care provider be able to access the patient's medical contact information including name, address and telephone number of a patient's primary care and specialist physicians.

Traditionally, each time a patient sees a doctor, or other medical care provider, the patient must fill out at least one medical history form prior to receiving treatment. The forms may be an initial history form for recording complete medical history when the patient had not been previously been treated by the medical care provider, or an update form for recording changes to the patient's medical history since the patient's last visit. In both cases, the patient completes the medical history information form relying on the patient's memory. The medical history information may not be accurate depending on many things including, a patient's recollection, a patient's understanding of his own medical condition, a patient's understanding of prior treatments received, as well as other factors that may lead to false, ambiguous or omitted medical history information.

In 1996, Congress enacted the Health Insurance Portability and Accountability Act (HIPAA). HIPAA gives the patient rights over his own medical history information, and contains rules on who may look at and receive the patient's medical information. The Congress called on the United States Department of Health & Human Services (HHS) to issue patient privacy protections as part of the HIPAA. Key provisions of the patient privacy protections involve a patient's access to his own medical records, limits on the use of a patient's medical information, and prohibitions on marketing the patient's medical information. Current abilities for the patient to access the patient's own medical history, particularly up-to-date medical information, is limited. The patient's access to the patient's own medical history is important because the access may lead to the patient determining existence of an error in the patient's medical history, or presence of a correct entry in the patient's history of which the patient himself was unaware.

The purpose of the protections issued by HHS is to ensure confidentiality, integrity and availability of electronically maintained records, as well as to protect against reasonably anticipated threats or hazards to security and integrity of the medical information and protect against illegal uses or disclosures of the information. In order to comply with HIPAA, it is important to have a system capable of accessing up-to-date medical history information while maintaining the confidentiality and privacy required by HIPAA. This may be accomplished by an ability for the patient to control the access, and the level of access, to the patient's medical history information, (thus having an ability to deny access to, or set a limit on the amount of, the medical information provided to particular medical providers, or others that may have limited access modules) at the time that medical treatment is sought, or by pre-authorization particularly in the event of an catastrophe or emergency. The need for particular elements of the patient's medical information may differ depending on the type of the medical treatment sought by the patient. For example, a primary care physician and a major specialist may require access to the patient's full medical history, while a podiatrist, a specialist in cosmetic surgery, a dentist or a pharmacist may require access to only limited medical history. The limitations on the medical history may be based on the type of the medical history (e.g., the patient may not wish the dentist or the podiatrist to access information related to the date a Pap Smear was last performed) or by most recent time period time (e.g., the patient may wish a pharmacist's access limited to prescriptions issued within the last six (6) months and to known allergies and contraindications). This scenario is particularly useful when the patient purchases prescriptions from different pharmacies, or when the patient requires the medical treatment when away from home.

In an emergency or other situation where a patient may not be able to give consent to access medical history at the time the medical treatment is needed due to lack of consciousness, incompetence and other reasons, it may be crucial for the medical care provider to be aware of the patient's medical history. Options for a medical care provider to access a medical history include, communicating with a contact, such as a family member of the patient, who has the access and can inform the medical care provider of the medical history of the patient, and determining that the patient had pre-authorized the access to his medical history, for such a situation. Determination of such pre-authorization could be made through the use of an item carried by the patient, such as a card with a magnetic strip or bar code and a Personal Identification Number (PIN) of the patient that can be matched on a centralized database.

In addition to the patient's condition changing with time, new information is disclosed regarding medications on a continuing basis. The new information may include additional side effects and reactions with other drugs that may be a contraindication in the use or continued use of a particular drug currently prescribed for the patient. Alternatively, a side effect or reaction may be corrected or removed for a particular drug, thus changing a drug that was previously contraindicated into a drug potentially beneficial to the patient. Thus, an important mechanism in providing for ongoing quality medical care is a system that tracks both the patient's history and the new information related to drugs, combined with a matching capability and automatic triggering of notices and warnings to the physician, the pharmacist and the patient. Additionally, whenever new information is detected about a drug, it may be important that an advisory mailer or e-mail to the patient be generated that provides the notice that new information has been released regarding a medication that the patient is taking, and suggests that the patient contact his physician to obtain this important information.

Mental illness or other medical conditions may render a person unsuitable to obtain certain government licenses and/or permits such as a permit to purchase a firearm or other potentially dangerous weapon. Each year, thousands of guns are sold to individuals who have experienced mental illness or other medical condition in one form or another. It may be important for the proper authorities to have the ability to access a warning flag related to an applicant's medical history indicating potential unsuitability. If the patient has been recently treated or is undergoing care, it may be crucial that the authorities be made aware that further investigation may be warranted. However, so as to avoid violating the applicant's privacy or confidentiality, no information may be given regarding the condition or history. The flag thus may provide notice to the authorities that further investigation into the suitability of the license or the permit applicant may be warranted. While the license or the permit may ultimately be issued, this gives the authorities the time and tools to properly investigate a potentially dangerous situation, and still preserve the privacy and the confidentiality rights under HIPAA.

Local, regional or nationwide catastrophes such has hurricanes, floods etc. may warrant the need for a data base of those affected. Federal agencies, e.g. FEMA, American Red Cross to mention a couple, work together but have no current common data base of information of those affected. The ability to generate a data base of those who are affected by such catastrophe, provide medicine in a timely manner, and notify emergency contact persons is needed.

The authority to access the patient's medical history may also be given to another person or entity that does not provide medical services or dispense drugs. This scenario is useful if the medical care provider does not have access to a system described herein, but knows the patient's contact. Also, the patient may specify that certain persons may access the medical history only with the permission of another person. Additionally, the medical history may be available in foreign languages to facilitate access in non-English speaking communities. There are many different scenarios where the authority to access the medical history, with or without the consent of another person, may be important. For example, the authority to access the patient's medical information may be given to the person identified as the patient's contact (e.g., spouse, friend, family member) so that the medical care provider of the patient may communicate with the patient's contact for the patient's medical history. Another example is one in which the authority to access and allow others to access the medical history of the child may best be placed with the child's parent, or legal guardian. In the case of divorced parents, the authority may be placed with both parents, a custodial parent, a dependent parent, a step-parent, a biological parent, a legal guardian or some combination thereof. This may be important when the patient is near his home or traveling away from home, perhaps in a different country, and when the patient is a child or an incompetent person.

Many physicians have converted or are converting to housing the medical history information in persistent electronic storage (Paperless Patient Charts) using their own systems. However, many of the physicians do not have the capability of converting their paper systems to their own electronic storage systems. It is important that the capability be made available to physicians to convert their paper files to the persistent electronic storage without the necessity of the physician implementing his own system. It may also be important if the use of said capability had the affect of providing simultaneously updating of the patient's information for more timely access by the other medical care providers, as well as eliminating duplicate data entry.

In current medical history databases, the patient's medical information is provided by the patient himself. It may be important both for the completeness and accuracy of the patient's medical history to have the up-to-date medical history provided directly by the physician or, alternatively, by a service made available to physicians for entering the medical history information.

Currently, the patient's medical information may be housed in persistent storage on a chip, known as a Smart Card. However, the Smart Card is difficult to maintain and be accurate. Additionally, a Smart Card Reader must be available to access the medical information from the Smart Card. Also, currently there are Internet based medical records, however such do not comply with HIPPA and in some systems data is entered by the patient not the physician. Allowing the patient to edit their own medical records, without the knowledge or consent of their attending physician places both the physician and patient at risk.

In order to provide similar benefits to military personnel, it is important that a system is adopted strictly for military uses whereby only Emergency Rooms would have access to a military file in the event of an emergency.

SUMMARY OF THE INVENTION

The present invention is directed to a method and system whereby medical information of individuals may be readily accessed by medical service providers (or other approved companies or agencies) while maintaining the appropriate level of confidentiality required by law.

In the preferred embodiment, a person or a family (hereinafter referred to individually or collectively as "patient") initially sets up his Internet Medical Information System (IMED) account with the medical care provider preferably the primary care physician by supplying initial medical history and patient profile information. The initial medical history generally includes a history of the treatment received by the patient, the diagnoses, the results of medical testing including lab tests, and medications prescribed. The patient profile information may include the patient's name, address and telephone numbers, picture, the patient's contact information, insurance information, immunization records, birth certificate, information related to the person or corporate business entity that may access the patient's medical information, and whether access by the person or the business entity may be subject to consent of another person or business entity, and the contact information of the other person or business entity. The patient typically enters the patient profile information one time and to the best of his knowledge, however, the profile information may subsequently be updated by other medical records and by the patient, via their doctor. The profile information collected preferably includes a finger scan by a finger print scanner, wherein four (4) scans are initially taken of the right index, right thumb, left index, left thumb in that order. The present system also allows other biometrics, such as a retinal scan, to be used to identify the patient. The finger scan, or retina scan, is used to determine pre-authorization primarily in cases of emergency, when the patient in unconscious, but can also be used in non-emergency situations for convenience.

The patient conveys the initial medical history and the patient profile information by filling out a pre-printed form that is entered into the present IMED system via a scanner, which has been programmed for IMED use. The form also contains an Authorization for Release of Protected Health Information wherein the patient authorizes the IMED to obtain further medical information about the patient for use by the IMED system, and a General Release whereby the client agrees to indemnify the IMED, all legal users of the IMED information including the medical care providers, medical care facilities, their successors or assigns for liability resulting from the use of information obtained from the IMED system. The purpose of this system is to save lives, however while efforts are made to provide accurate information, the accuracy cannot be guaranteed. Not all physicians will participate or keep the medical history as up to date as possible, at least not at first.

Once the patient's form is completed and signed, the patient is given a credit card style card with a metallic strip containing the UPC and a Personal Identification Number (PIN) to be used for normal access to the patient's medical history. This card may be issued by the medical care provider at the time the form is submitted or at a later time by a mailing to the patient.

When the patient seeks medical treatment, the patient controls the level of access to his medical history. The levels of access comprise: standard basic history; standard full history; emergency medical information; pharmaceutical information; and official government and/or agency information (e.g., law enforcement agencies for background of mental instability, American Red Cross, and FEMA during catastrophes).

The patient typically swipes his card, enters the PIN, selects a subject of the medical history (e.g., the patient himself or a dependent), and selects whether full or basic medical information is to be displayed to the medical care provider. A printout of the medical history will then occur. The patient has the ability to state descriptions of the current problem, when the symptoms first began, who referred the patient to the medical care provider, and other pertinent information.

The patient may then review and correct any errors that may be listed, sign the General Release indemnifying the medical care provider and the IMED from liability, and only then allow the access of the medical history by the medical care provider.

The equipment needed to facilitate this system includes a computer, at least one server to store the IMED modules, a card reader capable of reading magnetic strip cards currently in wide use and with connectivity to the computer, a fingerprint scanner, (or retina scanner), with connectivity to the computer, internet access, and optionally a printer with connectivity to the computer.

Additional functions of the system include providing the ability for the medical care provider such as the physician to maintain a more detailed paperless report. This functionality requires that the medical care provider's computer contain the additional capability of database functionality.

IMED can also be adapted to provide the same method and system functionality to other industries such as veterinary, Home Health Care, Hospice, rehabilitation and any other specialty field. In the IMED system, the primary physician can prescribe orders to a Hospice or Home Health Care through IMED. The Hospice or Home Health Care can acknowledge such orders being administered and note any changes or complications to the physician through the IMED module).

It is an object of the present invention to provide pre-authorized access to specific portions of a patient's medical history.

It is a further object of the present invention to allow the patient to decide which entities will have access, and how much access each entity will have, to their medical history.

BRIEF DESCRIPTION OF THE DRAWINGS

The invention of the present application will now be described in more detail with reference to the accompanying drawings, given only by way of example, in which.

DETAILED DESCRIPTION OF THE INVENTION

Figure 1:
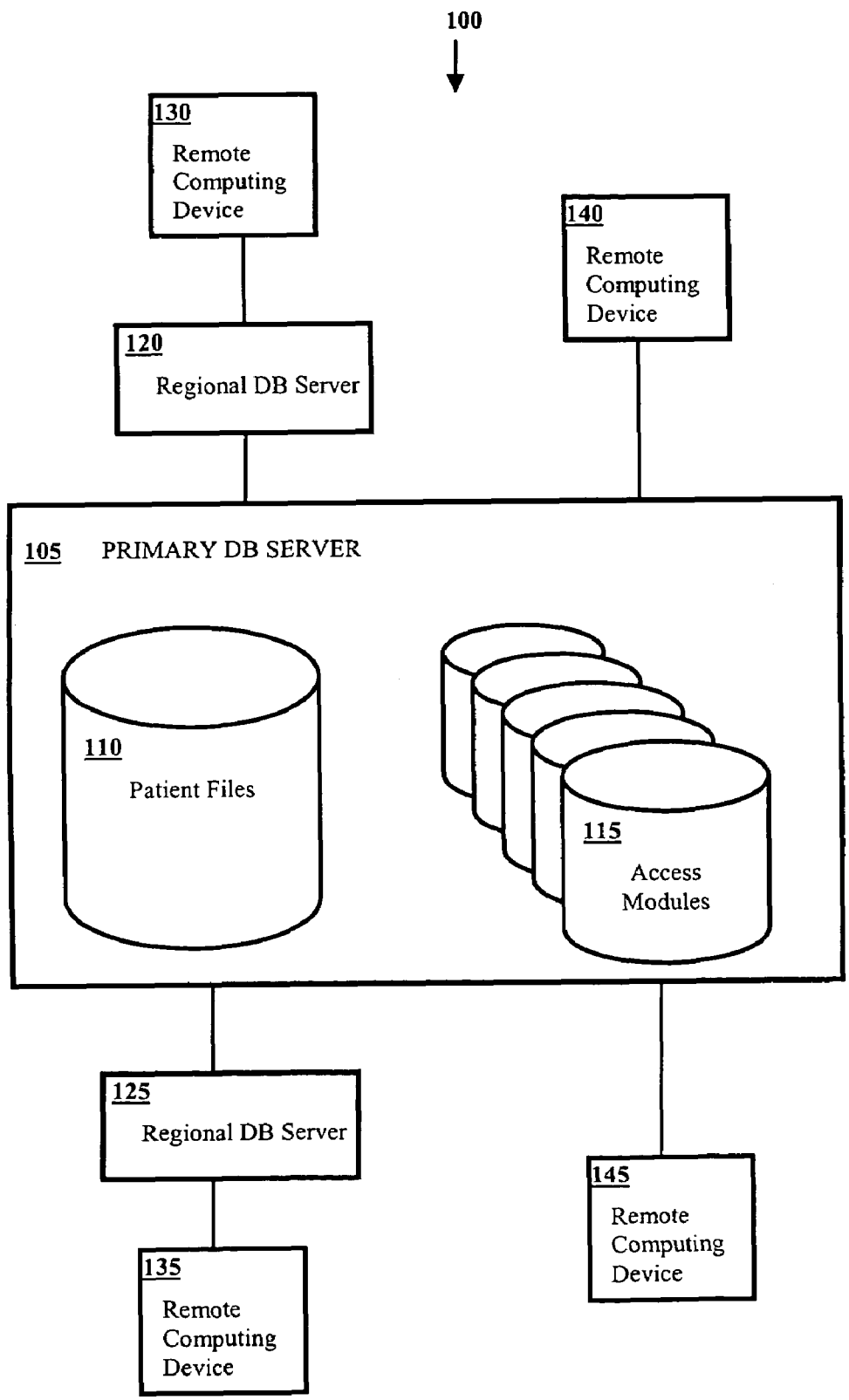
FIG. 1 is a block diagram of the preferred embodiment.

The present invention relates to a method and system for the establishment, maintenance and ubiquitous access to patients' medical information. The present Internet Medical Information System (IMED) is comprised of the mechanisms to access a database of medical histories via multiple access modules, processes to store medical information, and the processes to retrieve the medical information in whole or in part. The access to the patients' medical history is based on the pre-authorization by the patient.

Today when a patient walks in to a doctor's office, they are handed an update form and must rely on their memory to complete the form. The provided information may be accurate, or the patient may not remember one or several items that are important to the physician's treatment or diagnosis.

With the present IMED system, the patient comes in, swipes their ID card, enters their Personal Identification Number (PIN) and is automatically offered a choice of what history to give the physician (i.e. Basic, 3 Mo., 6 Mo., 12 Mo., or Full). If the patient is seeing their primary care physician, they may want a history of events since last seen. Access may also be obtained by way of a fingerprint scan.

The patient controls the level of access to his medical history, either allowing the access to his entire medical history maintained on IMED or to some subset of the information, at his own discretion. By allowing the patient to control the access to his own medical history either at the time the medical treatment is sought or by pre-authorization in the case of emergency, the present invention meets all HIPAA requirements ensuring the appropriate level of privacy and confidentiality related to the patient's medical information.

The present invention can be used by physicians, hospitals, emergency rooms, urgent care facilities, dental care providers, pharmacies and government offices and agencies. The system can also be used by the military medical community including emergency and urgent care of military personnel by civilian doctors. In addition, the patient may pre-authorize the access by any person anywhere in the world, as well as any corporate business entity such as a corporate guardian. Further, the patient may pre-authorize said access subject to the consent of any other person or corporate business entity in the world.

The present invention provides multiple access modules, each providing varying levels of access to patient information and thus providing privacy and confidentiality protections.

The IMED system can be used to perform automated matching of the patient's medical history with drug information so that warning notices may be automatically produced for physicians, pharmacists and patients when the attributes of a drug that a patient is taking changes.

In addition to summary medical history, IMED capabilities may include entering, storing and retrieving the detail medical history of the patient. The detail medical history may be used by physicians as their primary source of patient information (Paperless Patient Chart), and as the preferred method of the physician for entering the patient's medical treatment information. Said use eliminates duplicate data entry and allows for more timely access to of recent medical treatment by other medical care providers.

FIG. 1 is a block diagram of the preferred embodiment of the present IMED system 100. The primary database server 105 includes at least one database 110. The database 110 stores multiple patient files, with each patient file defining a medical history for a patient. The patient's medical history information is stored in multiple fields in the patient's file. After a patient authorizes a selected party to access his medical history, the selected party accesses the patient's file via one of multiple access modules 115. Every selected party is associated with one access module. Each of the access modules 115 includes an access file that dictates which fields the selected party may access. The selected parties are typically medical service providers or pharmacies, but the selected parties may also be a governmental agency, a charity, a school and the patient himself. The selected party uses a remote computing device 130, 135, 140 or 145, usually at the selected party's location, to access the patient's medical history. Some remote computing devices 140 & 145 can access the primary database server directly, via the Internet. However, other remote computing devices may use a regional database server 120 & 125 to access the patient's medical history. Regional database servers 120 & 125 can be placed in, or assigned to cover, highly populated regions. If required, a server could be located in each state, with state, regional and primary servers all being able to communicate with each other. In the event of a search, especially in an emergency, the search would start with local (State) server, then to the regional server, then to the primary server. In alternative embodiments, the access module associated with the selected party is also stored in the memory of the remote computing device.

Figure 2:
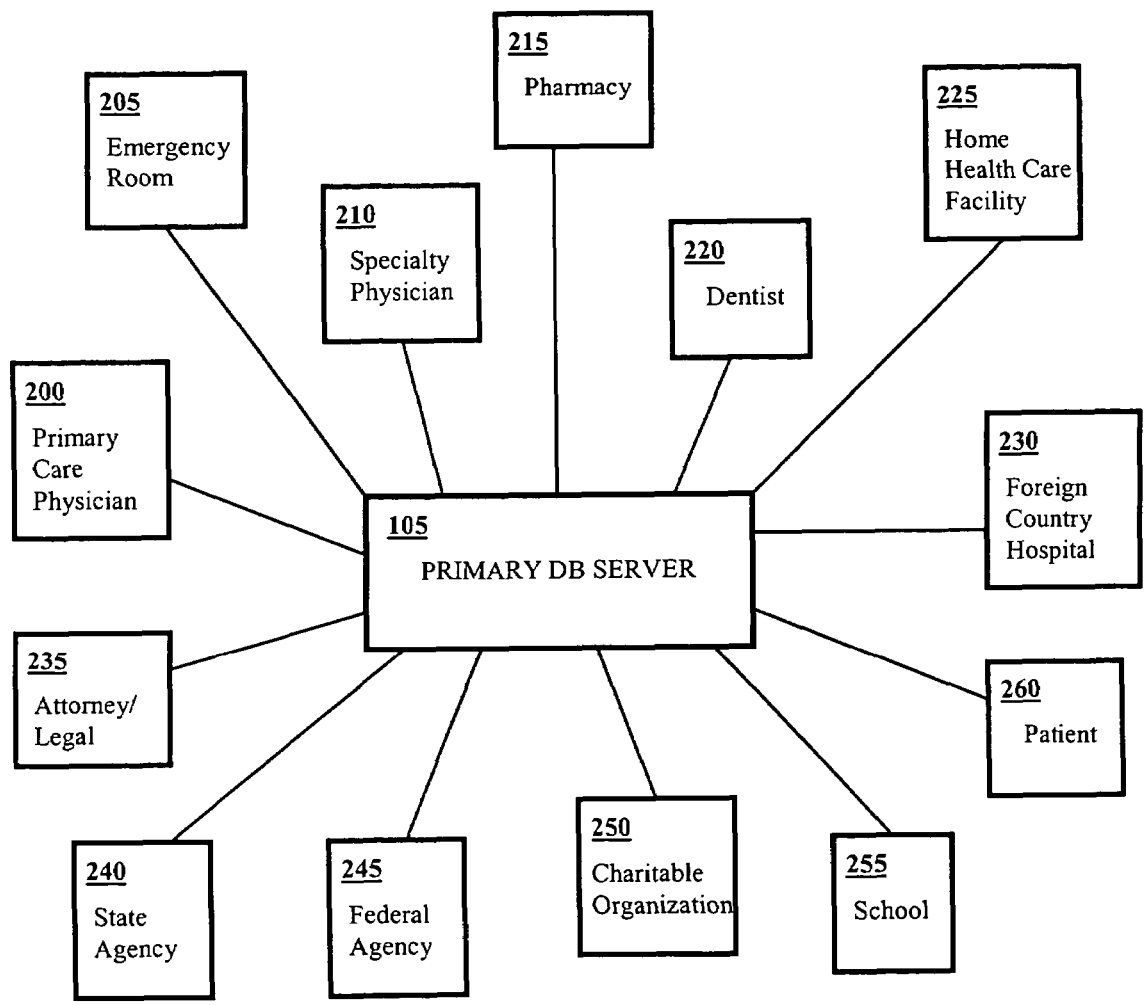
FIG. 2 is a conceptual block diagram showing selected parties that can be granted full or limited access, by the patient, to the patient's medical history.

FIG. 2 is a conceptual block diagram showing exemplary selected parties 200-260 that can be granted full or limited access to the patient's medical history, by the patient. Each selected party accesses medical histories in accordance with the limitations placed on the party by the access module associated with the selected party. In the preferred embodiment, the communication medium to the IMED database(s) is the Internet. In other embodiments, the communications medium can be any communication system including by way of example, dedicated communication lines, telephone networks, wireless data transmission systems, two-way cable systems, customized computer networks, interactive kiosk networks, automatic teller machine networks, interactive television networks, and the like. The Foreign Country Hospital 230 supports patients that are overseas and can provide medical information in multiple languages The selected party blocks illustrated in FIG. 1 are named for the users that can access the server 105.

The Primary Care Physician 200 is granted full access to the medical history. This provides the physician with the ability to give a full evaluation of the patient's condition and provide a care regiment that will not negatively affect the patient. The physician is also able to convert to an electronic patient information system (Paperless Patient Chart) if so desired. The access module associated with the Emergency Room 205 also allows full access to the patient's medical history. IMED may provide patent information to an emergency room that ends up saving the patient's life. A physician's lack of knowledge about the patient may prohibit timely life saving treatment. Further, critical patient information can prevent the treatment of certain medications that the patient does not tolerate or may be allergic. IMED can be accessed in the event of an emergency without further consent of the patient as they have authorized such access when they first created their patient file in the IMED system. Of course, the patient may amend what parties are given access at any time. The present system is well equipped for dealing with emergency situations. When a patient is unconscious the patient's finger can be scanned in order to identify the patient and access his medical history. The system will provide the physician immediately with critical medical information along with the contact information of the primary care physician and family members.

The access modules associated with the State and Federal Agency 240 & 245 parties allow government authorities to inquire as to the suitability of a person for licensing and permits. Each year, thousands of guns are sold to individuals who have experienced mental illness in one form or another. Most of these people experienced a traumatic situation that soon passes, whereby only a temporary treatment occurs and the patient is perfectly normal. Others however, experience ongoing treatment and may not be suitable at a particular time to purchase a firearm, or obtain another type of license, passport etc. IMED allows the proper authorities to ascertain whether or not a person desiring to purchase a firearm has been diagnosed with a mental illness. If a patient has been recently treated or is undergoing mental health care, a code will be issued that simply advises further medical follow up is suggested and the patient's physician information will be issued. In the preferred embodiment, no other patient information will be given to the government agency. A flag in the module will allow the authorities to conduct a proper investigation into the gun application. While the permit may ultimately be issued, the IMED system gives the authorities the time and tools to properly investigate and perhaps prevent a potentially dangerous situation. These modules would also allow the Federal Emergency Management Agency (FEMA), and related charities such as the American Red Cross, to have access to critical patient information in the event of a crisis or natural disaster.

The access module associated with the Pharmacy 215 allows the pharmacy to inquire into prescriptions that have been issued to the patient over the last twelve (12) months, known allergies and contraindications, as well as to update IMED or the pharmacist with information related to the prescriptions, allergies, and contraindications. Additionally, the present system supports the dissemination of new information about a drug such as additional side effects, reactions with other drugs and other contraindications. The present system can automatically match patients with certain prescription issued to them, detect instances where newly discovered contraindications have become known or prior contraindications have been removed, and send a warning such as an email to the patients' primary care physician and/or pharmacy regarding the newly discovered contraindication.

The access modules associated with a Specialist Physician 210, a Dentist 220, and a Home Health Care Facility 225 allow a medical care specialist, a dental health care provider, and a home health care provider to inquire into the medical history information that is pertinent to the patient's care under the medical care specialist, the dental health care provider, and the home health care provider, respectively. The IMED system also allows for the update the patient files regarding diagnosis and treatment provided by said medical care specialist and said health care provided.

The number access modules in the IMED system is not limited and other modules can be added as needed. For example, a module for paramedics that allows patient information to be sent to an ambulance would be useful. Further, an access module for police that allows pertinent information to be sent directly to squad cars would also be useful.

Figure 3:
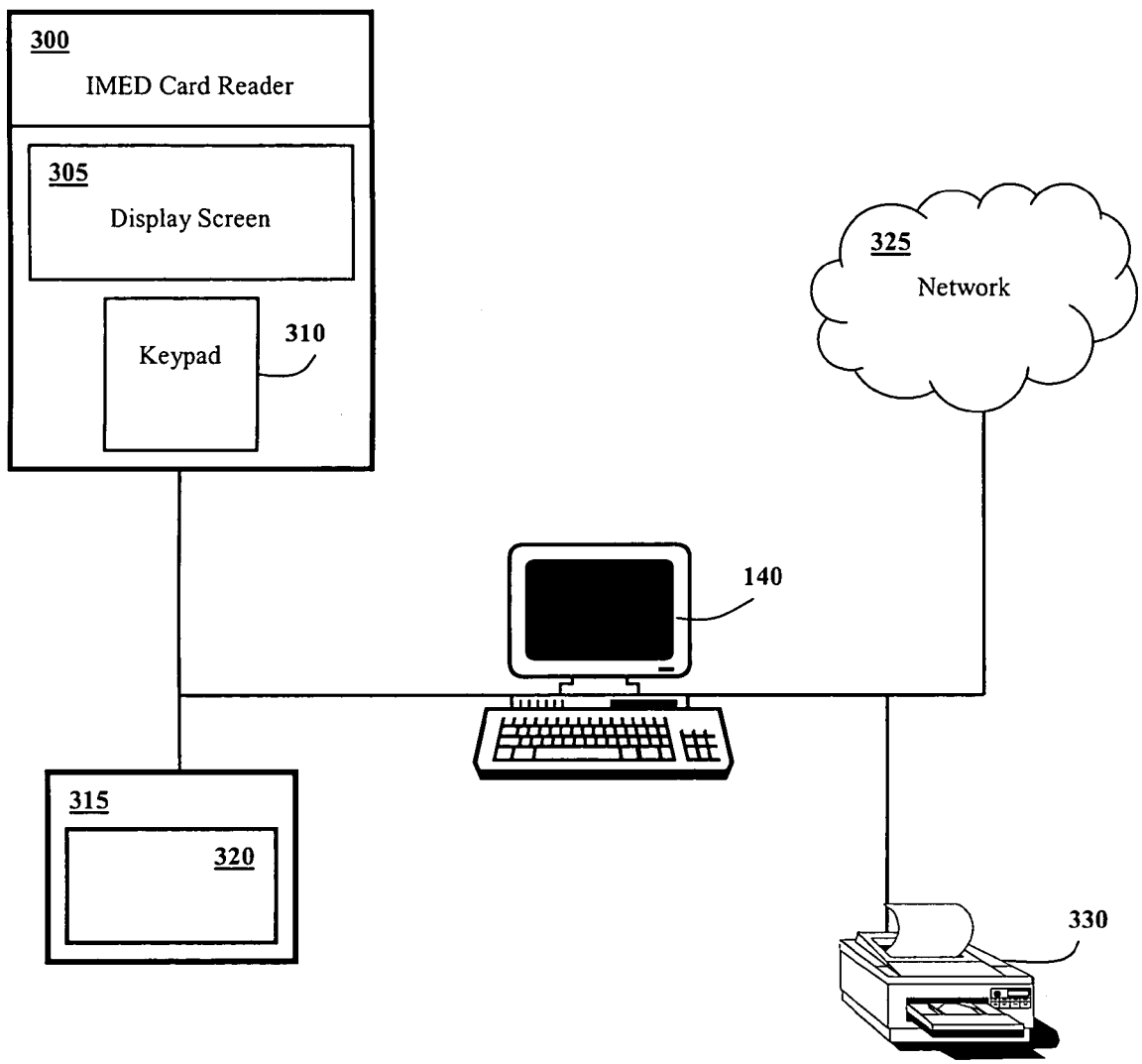
FIG. 3 shows exemplary hardware that is used by a selected party in the preferred embodiment.

FIG. 3 shows exemplary hardware that can be used by a selected party, in the preferred embodiment, to identify a patient and access at least part of the patient's medical history. The remote computing device, or computer, 140 is electrically connected to an identification device, either an IMED card reader 300 or a biometric reading device 315, such as a fingerprint scanner, which is used to identify the patient. Of course, the biometric reading device may also be any of the currently known retinal scanners. The computer 140 is also electrically connected to the Internet 325 and a printer 330. The IMED Card Reader 300 comprises: a credit card style reader; a display screen 305; and, a keypad 310. The credit card style reader allows for the reading of a barcode or electromagnetic strip on the patient's IMED I.D. Card. The display screen 305 and keypad 310 allow the patient to further limit the level of access granted to the selected party. The patient's medical history includes basic history, full history, history from the last thirty (30), sixty (60), or ninety (90) days. The medical history can be obtained from the participating medical care providers only when the patient so authorizes. The medical history generally includes the patient's full name, address, telephone numbers (home, work, cell), social security number, date of birth, responsible party information (applicable when the person with the power to control access is not the patient himself, such as with a child), primary care physician, date of last visit to any physician, pharmacy information, emergency contact, insurance information, a Living Will, including Do Not Resuscitate (DNR) instructions, and other information such as immunization records, birth certificate(s) and organ donor authorization.

If the basic form is selected, a limited amount of medical information may be provided including blood type, special notations, allergies, current medications, surgery history and dates, temporary medications and current Major Medical conditions. The intent of the standard basic set of elements is to allow the medical care provider to quickly and efficiently obtain and review the basic medical history of the patient. If the full history report is selected, the report comprises the full medical history for the prior twelve (12) months. The medical care provider may print out additional information, including entire history if needed, at the discretion of the medical care provider. The reports may be in major sequence order by disease, illnesses, injury, routine check-up, elective medical treatment (e.g., cosmetic surgery) and OB-GYN records, and minor sequence order by date of last treatment date, treatment, medications prescribed. The basic report would always be a part of the history report for the patient to review.

The medical care providers and other entities where the medical care is provided such as ambulances and hospitals, are provided with card readers 300 and biometric reading device 315, which are used to determine the patient's pre-authorization of access, and the level thereof, to the medical history of the patient. This allows the medical care provider access to the patient's medical history based upon the patient's pre-authorization, and thus the access to the medical history is in keeping with the requirements of HIPAA. Additionally, the medical care provider may update the medical history of the patient at the time the medical care is provided.

Figure 4:
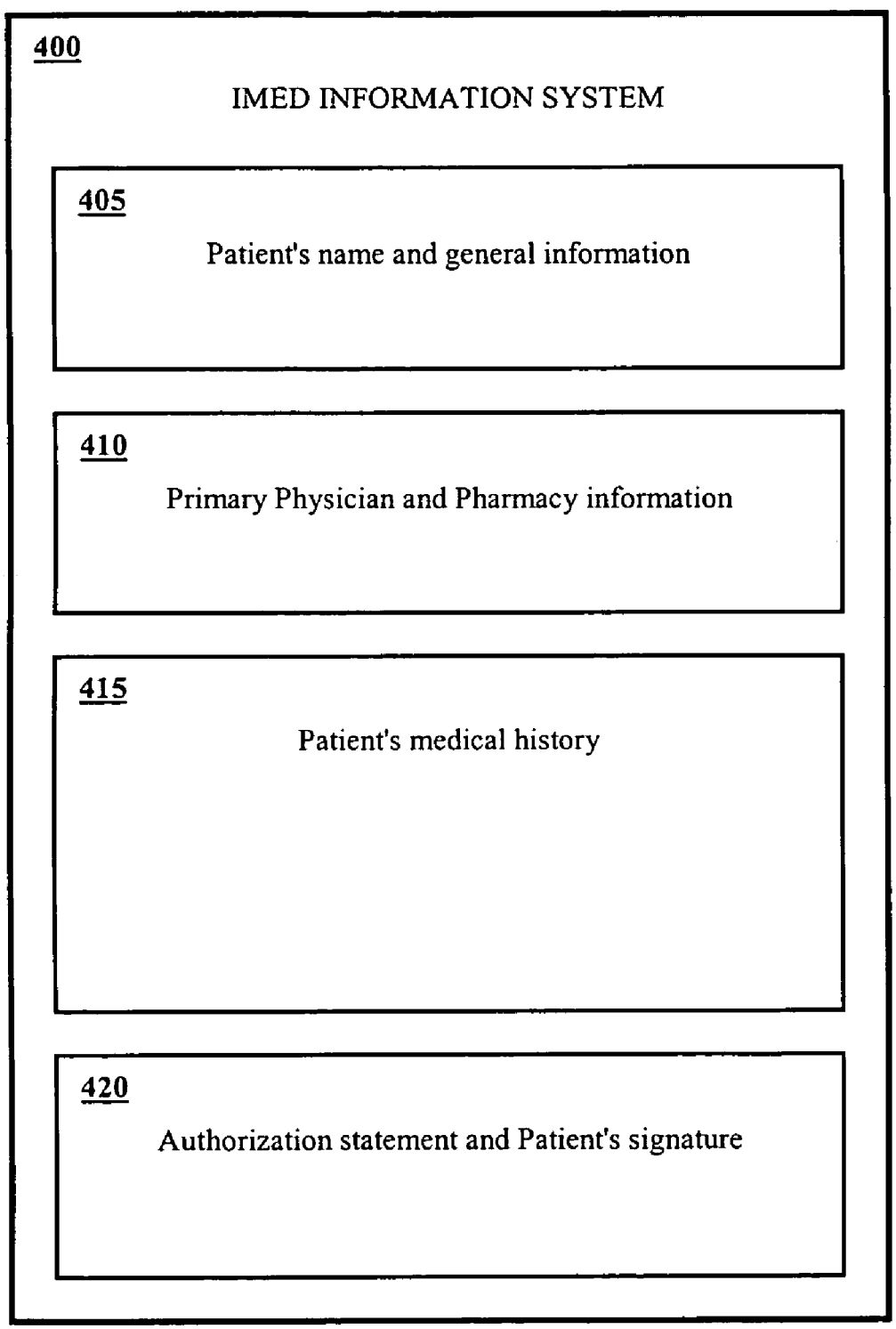
FIG. 4 is an exemplary form that a patient can use to build their medical history and to pre-authorize access to the history.

FIG. 4 is an exemplary form 400 that a patient can use to build their medical history and to pre-authorize access to the history. Physicians may also use a similar form to help build the patients medical history. The form 400 can be filled out and submitted on-line, i.e., on a computer, or the form 400 can be printed and filled out by hand, in writing. Section 405 allows the patient to enter general information about the patient, such as name, address, SSN and date of birth. Section 410 allows for entry of the patient's doctor and pharmacy information. Section 415 preferably prompts the patient for information regarding illnesses, diseases, injuries, surgeries, medications, allergies, immunizations and other medical history information. Section 420 includes an authorization statement, wherein the patient authorizes later access to his medical record. The authorization also preferably includes a list of which portions of the patient's medical history the selected party may access. Section 420 includes a signature block for a handwritten or electronic signature of the patient. Form 400 is stored electronically by the IMED system.

Figure 5:
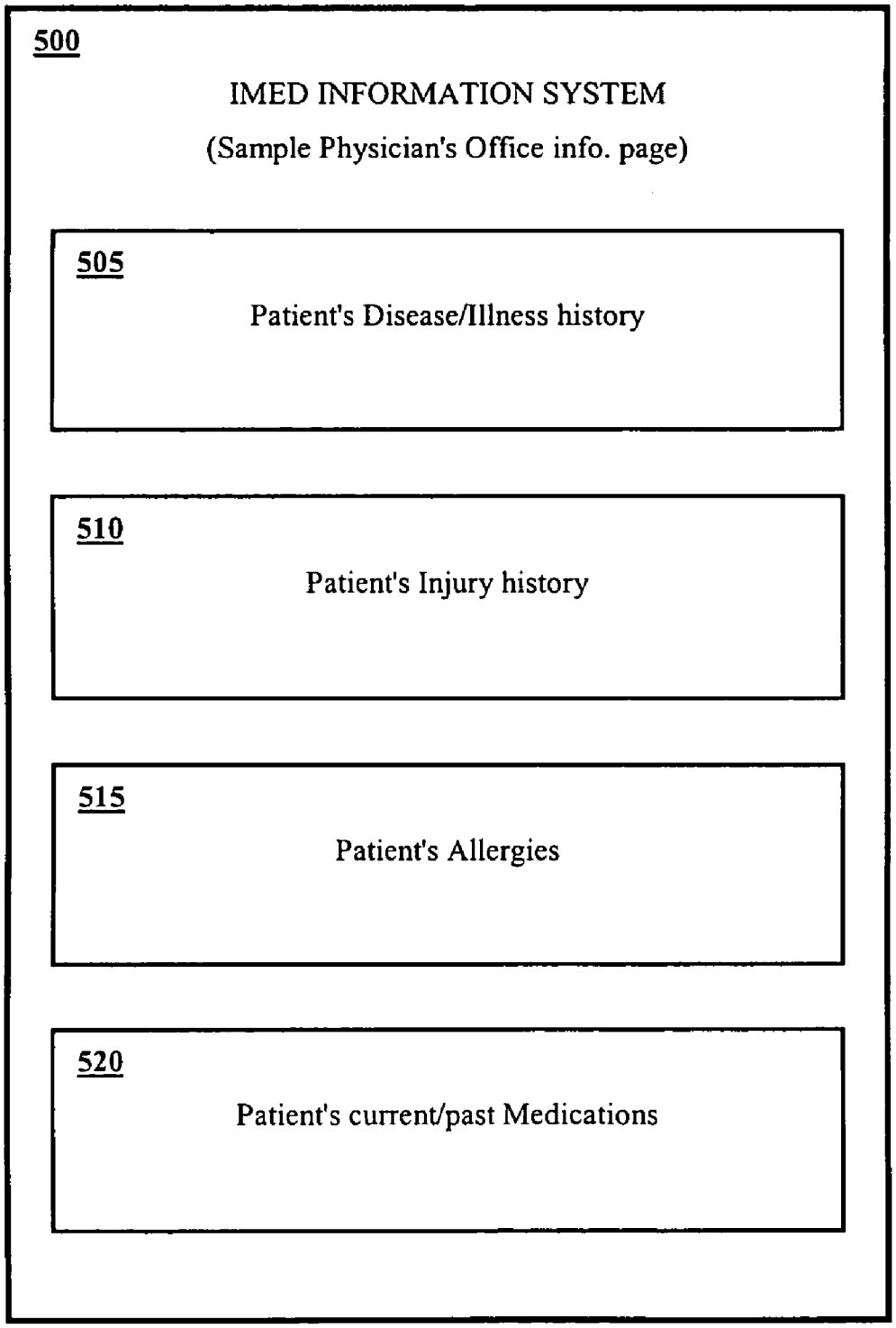
FIG. 5 is an exemplary medical history screen that can be shown to a selected party that has been authorized, by the patient, to access the history; and, FIG. 6 is an exemplary report, generated during a catastrophe, and sent to FEMA or the American Red Cross.

FIG. 5 is an exemplary medical history screen 500 that can be shown to a selected party that has been authorized, by the patient, to access the history. The history screen 500 breaks the patient's medical history into distinct sections so the doctor can easily locate the information he is looking for. Section 505 includes all diseases and illnesses the patient has suffered from and includes information regarding complaints, diagnosis and treatment for each disease and illness. Section 510 includes information relating to all injuries suffered by the patient. Section 510 also includes information relating to dates of the injuries, diagnosis and treatment. Section 515 lists all known allergies of the patient. Section 520 provides information relating to past and current medications of the patient. Of course, other screens with other medical history can be provided by the present system. The information that can be displayed is only limited by the access module associated with the selected party.

FIG. 6 is an exemplary report 600 that can be generated by IMED during a catastrophe and sent to FEMA, the American Red Cross, or other agency/charity. Section 605 shows the name and current location of the patient. The IMED system advantageously allows patients that have lost everything to still be able to identify themselves by using the patient's fingerprint or retinal scan to gain entry into the system. The current location of the patient, in section 605, is automatically generated and is based on the location where the patient's identifying scan occurred. Section 605 preferably includes the name, address and telephone number of the shelter. Section 610 provides the relief organization with a 5-day medical requirement of the patient, which alerts the organization to the immediate medical needs of the patient. The IMED system is also able to order necessary medications for the patient, via the access module associated with the patient's pharmacy. Of course, if the patient have been moved far away from his regular pharmacy, another closer pharmacy may also be used. Section 615 provides the relief organization with the basic medical history of the patient. This section includes provides general information, such as address, allergies and blood type, to the organization which makes caring for the patient easier. Section 620 includes emergency contact information, such as next of kin. In the preferred embodiment, when the patient identifies himself via a FEMA/Red Cross access module, e-mail notices are automatically generated and sent to the emergency contacts. The e-mails include the name of the patient, the time and date of contact, and the name, address and phone number of the facility where the patient was scanned. The relief organization may also use the IMED system to contact other agencies, such as Medicare and the Social Security Administration, in order to gain further benefits for the patient.

The foregoing description of the specific embodiments will so fully reveal the general nature of the invention that others can, by applying current knowledge, readily modify and/or adapt for various applications such specific embodiments without departing from the generic concept. Therefore, such adaptations and modifications should and are intended to be comprehended within the meaning and range of equivalents of the disclosed embodiments. It is to be understood that the phraseology of terminology employed herein is for the purpose of description and not of limitation.

I claim:

1. A system for creating, maintaining and accessing medical histories and, in emergencies, for providing pre-authorized access to the medical histories, wherein patients pre-authorize selected parties to access the histories and wherein access to the histories is limited for many of the selected parties, the system comprising:
   at least one server, which has stored therein:
      at least one database, the at least one database, storing multiple patient files, wherein each patient file is associated with a patient and contains patient information, wherein the patient information defines a medical history of the associated patient, the patient information being stored in multiple fields within each patient file;
      the at least one server also having stored therein multiple access modules, wherein each access module is associated with a selected party and at least one patient file, further wherein each access module comprises multiple data files, and at least one of the data files is an access file that contains limiting information that dictates an amount of the patient's medical history the associated selected party may access;
   a network, wherein the at least one sever is connected to the network;
   a computer, wherein the computer is associated with an access module and is connected to the network, wherein the selected party associated with the access module is able to gain access to the at least one patient file in the server in accordance with the access file, and wherein the patients can use the computer to authorize access to their medical histories without the aid of an identification card or a smart card; and,
   an identification device that is connected to the computer, capable of identifying the patient upon physical interaction with the patient, even when the patient is unconscious, and wherein upon identification, the selected party is able to access the patient's medical history in the server in accordance with the associated access module.

2. The system of claim 1, wherein the identification device is a biometric reading device, including a fingerprint scanner and a retina scanner.

3. The system of claim 1, wherein the identification device is an electro-magnetic card reader capable of reading a card with an electro-magnetic strip, and wherein only connection related information is stored on the card that assists in connection to the server and access to the files and modules stored in the server.

4. The system of claim 1, wherein at least one of the multiple data files is an administration file that provides an interface for the patient and the selected party and assists in creating the patient files and associating at least one access module to each patient file.

5. The system of claim 4, wherein the administration file also provides an interface for the patient and the selected party to update the patient's medical history.

6. The system of claim 1, wherein at least some patient information and at least one access module are stored on the computer.

7. The system of claim 1, further comprising a printer that is attached to the computer, and wherein at least one of the multiple data files is a forms file that includes at least one authorization form that can be printed on the printer, the authorization form having a signature area for the patient to sign.

8. The system of claim 7, wherein the authorization form includes an authorization statement, authorizing access to at least a portion of the patient's medical history.

9. The system of claim 1, wherein the selected party is a primary care physician or emergency room and the access modules allow full access to all of the patient's medical history.

10. The system of claim 1, wherein the selected party is a dentist office and the access module limits access, to the patient's medical history, to information that is required by a dentist.

11. The system of claim 1, wherein the selected party is a pharmacy and the access module limits access, to the patient's medical history, to information regarding medications and allergies.

12. The system of claim 1, wherein the selected party is medical specialist and the access module limits access, to the patient's medical history, to information required by the medical specialist.

13. The system of claim 1, wherein the selected party is a state agency, including a firearm ownership registration agency, and the access module limits access to patient information related to mental illness.

14. The system of claim 1, wherein the selected party is a school and the access module limits access to patient information regarding immunization records.

15. The system of claim 1, wherein the selected party is a law office and the access module limits access to patient information required by the law office, including living wills, including do not resuscitate (DNR) orders, and information the law office needs to prosecute a personal injury case and a workman's compensation case.

16. The system of claim 1, wherein the patient information includes name, address, phone number(s), date of birth, a picture, primary care doctor's name and phone number(s), pharmacy information, medication information and allergy information.

17. The system of claim 1, wherein the patient information includes in-case-of-emergency contact information, insurance information, blood type, disease/illness information, lab test results, and past 30, 60, and 90 day sub-histories.

18. The system of claim 17, wherein the identification device allows the patient to further limit the medical history that is displayed on the computer to a past 30, 60 or 90 sub-history.

19. The system of claim 1, wherein the selected party is a federal agency, including the federal emergency management agency, and the access module limits access to patient information regarding current medical condition, current medications, allergies, emergency contact information and location information.

* * * * *